United States Patent
Abraham et al.

(10) Patent No.: US 6,572,650 B1
(45) Date of Patent: Jun. 3, 2003

(54) BIOENGINEERED VASCULAR GRAFT SUPPORT PROSTHESES

(75) Inventors: Ginger A. Abraham, Braintree, MA (US); Robert M. Carr, Jr., West Roxbury, MA (US); Tam Huynh, Canton, MA (US); Otto Per Hagen, Durham, NC (US); Mark Davies, Rochester, NY (US)

(73) Assignees: Organogenesis Inc., Canton, MA (US); Duke University School of Medicine, Durham, NC (US)

( * ) Notice: Subject to any disclaimer, the term of this patent is extended or adjusted under 35 U.S.C. 154(b) by 0 days.

(21) Appl. No.: 09/719,072

(22) PCT Filed: Jun. 4, 1999

(86) PCT No.: PCT/US99/12500

§ 371 (c)(1),
(2), (4) Date: Jun. 11, 2001

(87) PCT Pub. No.: WO99/62427

PCT Pub. Date: Dec. 9, 1999

(51) Int. Cl.[7] .................................. A61F 2/06
(52) U.S. Cl. .............. 623/1.38; 623/1.44; 623/1.47
(58) Field of Search ................... 623/1.38, 1.14, 623/1.27, 1.28, 1.24, 1.25, 1.44–1.54

(56) References Cited

U.S. PATENT DOCUMENTS

| | | |
|---|---|---|
| 3,272,204 A | 9/1966 | Artandi et al. |
| 3,562,820 A | 2/1971 | Braun |
| 3,974,526 A | 8/1976 | Dardik et al. |
| 4,082,507 A | 4/1978 | Sawyer |
| 4,252,759 A | 2/1981 | Yannas et al. |
| 4,319,363 A | 3/1982 | Ketharanathan |
| 4,323,525 A | 4/1982 | Bornat |
| 4,420,339 A | 12/1983 | Kato |
| 4,475,972 A | 10/1984 | Wong |
| 4,502,159 A | 3/1985 | Woodroof et al. |
| 4,539,716 A | 9/1985 | Bell |
| 4,597,762 A | 7/1986 | Walter et al. |
| 4,629,458 A | 12/1986 | Pinchuk |
| 4,787,900 A | 11/1988 | Yannas |
| 4,801,299 A | 1/1989 | Brendel et al. |
| 4,814,120 A | 3/1989 | Huc et al. |
| 4,822,361 A | 4/1989 | Okita et al. |
| 4,842,575 A | 6/1989 | Hoffman, Jr. et al. |
| 4,863,668 A * | 9/1989 | Griffiths et al. ............. 264/233 |
| 4,889,120 A | 12/1989 | Gordon |
| 4,902,289 A | 2/1990 | Yannas |
| 4,902,290 A | 2/1990 | Fleckenstein et al. |
| 4,902,508 A | 2/1990 | Badylak et al. |
| 4,923,380 A | 5/1990 | Huc et al. |
| 4,956,178 A | 9/1990 | Badylak et al. |
| 5,002,583 A | 3/1991 | Pitaru et al. |
| 5,024,671 A | 6/1991 | Tu et al. |
| 5,026,381 A | 6/1991 | Li |

(List continued on next page.)

FOREIGN PATENT DOCUMENTS

| | | |
|---|---|---|
| EP | 0 397 500 A2 | 11/1990 |
| EP | 0 493 788 A1 | 7/1992 |
| GB | 2153235 A | 8/1985 |
| WO | WO89/10100 | 11/1989 |
| WO | WO98/25544 | 6/1998 |
| WO | WO98/25545 | 6/1998 |
| WO | WO98/25546 | 6/1998 |
| WO | WO98/44969 | 10/1998 |

OTHER PUBLICATIONS

Matsumoto et al., *Surgery*, 60(3): 739–743 (1966).
Egusa, *Acta Med. Okayama* 22: 153–165, (1968).
Fraser et al., *Arch Surg.*, 96: 378–385 (1968).
Lawler, Jr. et al., *The American Journal of Surgery*, 122: 517–519 (1971).
Staros, *Biochem.*, 21: 3950–55 (1982).
Dagan et al., *Vascular Surgery*, Jul./Aug.: 199–206 (1983).
Broll et al., *Eur. Surg. Res.* 18: 390–396 (1986).
American National Standard for Vascular Graft Prostheses, Association for the Advancement of Medical Instrumentation, approved Jul. 7, 1986.
Zwolak et al., *J. Vasc. Surg.*, 5: 126–36, (1987).
Haimovici, *Vascular Surgery*, 3rd *Edition*: 287–292 (1989).
Silverman, *Sterilization and Preservation by Ionizing Irradiation* in Disinfection, Sterilization, and Preservation, 4th Edition, Ch. 32: 566–579 (1991).
Schwartz et al., *J. Vasc. Surg.* 15: 176–186 (1992).
Wyler et al., *Journal of Biomedical Materials Research*, 26: 1141–1146 (1992).
Abbott et al., *Journal of Vascular Surgery*, 17 (4): 746–756 (1993).
Hiles et al., *Journal of Biomed. Materials Res.*, 27: 139–144 (1993).
Onohara et al., *J. Surg Res.*, 55: 344–50, (1993).
Carr et al., The Study of the Release of Benzalkonium–Heparin Complex from an Absorbable Synthetic Collagen Graft, The 20th Annual Meeting of the Society for Biomaterials, Apr. 5–9, 1994.
Termin et al., *Remodeling of an Absorable Synthetic Collagen Graft: Long Term Implant Histology*, The 20th Annual Meeting of the Society for Biomaterials, Apr. 5–9, 1994.
Dorbin, *Hypertension*, 26: 38–43, (1995).
Kraiss et al., *Circ. Res.*, 79: 45–53, (1996).
Takahashi and Berk, *Journal of Clinical Investigation*, 98: 2623–2631 (1996).
Mehta et al., *Nature Medicine*, 4: 235–39 (1998).

*Primary Examiner*—Corrine McDermott
*Assistant Examiner*—Hieu Phan
(74) *Attorney, Agent, or Firm*—Hale and Dorr LLP

(57) ABSTRACT

The invention is directed to bioengineered vascular graft support prostheses prepared from cleaned tissue material derived from animal sources. The bioengineered graft prostheses of the invention are prepared using methods that preserve cell compatibility, strength, and bioremodelability of the processed tissue matrix. The bioengineered graft prostheses are used for implantation, repair, or for use in a mammalian host.

3 Claims, No Drawings

U.S. PATENT DOCUMENTS

| | | |
|---|---|---|
| 5,037,377 A | 8/1991 | Alonso |
| 5,061,276 A | 10/1991 | Tu et al. |
| 5,084,065 A | 1/1992 | Weldon et al. |
| 5,106,949 A | 4/1992 | Kemp et al. |
| 5,108,424 A | 4/1992 | Hoffman, Jr. et al. |
| 5,131,908 A | 7/1992 | Dardik et al. |
| 5,197,977 A | 3/1993 | Hoffman, Jr. et al. |
| 5,256,418 A | 10/1993 | Kemp et al. |
| 5,263,983 A | 11/1993 | Yoshizato et al. |
| 5,374,515 A | 12/1994 | Parenteau et al. |
| 5,376,110 A | 12/1994 | Tu et al. |
| 5,376,376 A | 12/1994 | Li |
| 5,378,469 A | 1/1995 | Kemp et al. |
| 5,460,962 A | 10/1995 | Kemp |
| 5,571,216 A | 11/1996 | Anderson |
| 5,733,337 A * | 3/1998 | Carr et al. .................. 435/325 |
| 5,776,182 A | 7/1998 | Bruchman et al. |
| 5,824,063 A | 10/1998 | Cox |
| 5,851,230 A | 12/1998 | Weadock et al. |
| 5,879,383 A | 3/1999 | Bruchman et al. |
| 5,948,654 A | 9/1999 | Tranquillo et al. |
| 5,968,092 A | 10/1999 | Buscemi et al. |
| 5,993,844 A | 11/1999 | Abraham et al. |
| 6,126,686 A | 10/2000 | Badylak et al. |
| 6,187,039 B1 | 2/2001 | Hiles et al. |
| 6,206,931 B1 | 3/2001 | Cook et al. |

* cited by examiner

BIOENGINEERED VASCULAR GRAFT SUPPORT PROSTHESES

FIELD OF THE INVENTION

This invention is in the field of tissue engineering. The invention is directed to bioengineered graft prostheses prepared from cleaned tissue material derived from animal sources. The bioengineered graft prostheses of the invention are prepared using methods that preserve cell compatibility, strength, and bioremodelability of the processed tissue matrix. The bioengineered graft prostheses are used for implantation, repair, or for use in a mammalian host.

BRIEF DESCRIPTION OF THE BACKGROUND OF THE INVENTION

The field of tissue engineering combines the methods of engineering with the principles of life science to understand the structural and functional relationships in normal and pathological mammalian tissues. The goal of tissue engineering is the development and ultimate application of biological substitutes to restore, maintain, and improve tissue functions.

Collagen is the principal structural protein in the body and constitutes approximately one-third of the total body protein. It comprises most of the organic matter of the skin, tendons, bones, and teeth and occurs as fibrous inclusions in most other body structures. Some of the properties of collagen are its high tensile strength; its low antigenicity, due in part to masking of potential antigenic determinants by the helical structure; and its low extensibility, semipermeability, and solubility. Furthermore, collagen is a natural substance for cell adhesion. These properties and others make collagen a suitable material for tissue engineering and manufacture of implantable biological substitutes and bioremodelable prostheses.

Methods for obtaining collagenous tissue and tissue structures from explanted mammalian tissues and processes for constructing prosthesis from the tissue, have been widely investigated for surgical repair or for tissue or organ replacement. It is a continuing goal of researchers to develop prostheses that can successfully be used to replace or repair mammalian tissue.

SUMMARY OF THE INVENTION

Biologically-derived collagenous materials such as the intestinal submucosa have been proposed by a many of investigators for use in tissue repair or replacement. Methods for mechanical and chemical processing of the proximal porcine jejunum to generate a single, acellular layer of intestinal collagen (ICL) that can be used to form laminates for bioprosthetic applications are disclosed. The processing removes cells and cellular debris while maintaining the native collagen structure. The resulting sheet of processed tissue matrix is used to manufacture multi-layered laminated constructs with desired specifications. We have investigated the efficacy of laminated patches for soft tissue repair as well as the use of entubated ICL as a support for vascular grafts. This material provides the necessary physical support and is able to integrate into the surrounding native tissue and become infiltrated with host cells. In vivo remodeling does not compromise mechanical integrity. Intrinsic and functional properties of the implant, such as the modulus of elasticity, suture retention and UTS are important parameters which can be manipulated for specific requirements by varying the number of ICL layers and the crosslinking conditions.

DETAILED DESCRIPTION OF THE INVENTION

This invention is directed to a tissue engineered prostheses, which, when implanted into a mammalian host, can serve as a functioning repair, augmentation, or replacement body part or tissue structure, and will undergo controlled biodegradation occurring concomitantly with remodeling by the host's cells. The prosthesis of this invention, when used as a replacement tissue, thus has dual properties: First, it functions as a substitute body part, and second, while still functioning as a substitute body part, it functions as a remodeling template for the ingrowth of host cells. In order to do this, the prosthetic material of this invention is a processed tissue matrix developed from mammalian derived collagenous tissue that is able to be bonded to itself or another processed tissue matrix to form a prosthesis for grafting to a patient.

The invention is directed toward methods for making tissue engineered prostheses from cleaned tissue material where the methods do not require adhesives, sutures, or staples to bond the layers together while maintaining the bioremodelability of the prostheses. The terms, "processed tissue matrix" and "processed tissue material", mean native, normally cellular tissue that has been procured from an animal source, preferably a mammal, and mechanically cleaned of attendant tissues and chemically cleaned of cells, cellular debris, and rendered substantially free of non-collagenous extracellular matrix components. The processed tissue matrix, while substantially free of non-collagenous components, maintains much of its native matrix structure, strength, and shape. Preferred compositions for preparing the bioengineered grafts of the invention are animal tissues comprising collagen, including, but not limited to: intestine, fascia lata, pericardium, dura mater, and other flat or planar structured tissues that comprise a collagenous tissue matrix. The planar structure of these tissue matrices makes them able to be easily cleaned, manipulated, and assembled in a way to prepare the bioengineered grafts of the invention. Other suitable collagenous tissue sources with the same flat sheet structure and matrix composition may be identified by the skilled artisan in other animal sources.

A more preferred composition for preparing the bioengineered grafts of the invention is an intestinal collagen layer derived from the tunica submucosa of small intestine. Suitable sources for small intestine are mammalian organisms such as human, cow, pig, sheep, dog, goat, or horse while small intestine of pig is the preferred source.

The most preferred composition for preparing the prosthesis of the invention is a processed intestinal collagen layer derived the tunica submucosa of porcine small intestine. To obtain the processed intestinal collagen layer, the small intestine of a pig is harvested and attendant mesenteric tissues are grossly dissected from the intestine. The tunica submucosa is preferably separated, or delaminated, from the other layers of the small intestine by mechanically squeezing the raw intestinal material between opposing rollers to remove the muscular layers (tunica muscularis) and the mucosa (tunica mucosa). The tunica submucosa of the small intestine is harder and stiffer than the surrounding tissue, and the rollers squeeze the softer components from the submucosa. In the examples that follow, the tunica submucosa was mechanically harvested from porcine small intestine using a Bitterling gut cleaning machine and then chemically cleaned to yield a cleaned tissue matrix. This mechanically and chemically cleaned intestinal collagen layer is herein referred to as "ICL".

The processed ICL is essentially acellular telopeptide collagen, about 93% by weight dry, with less than about 5% dry weight glycoproteins, glycosaminoglycans, proteoglycans, lipids, non-collagenous proteins and nucleic acids such as DNA and RNA and is substantially free of cells and cellular debris. The processed ICL retains much of its matrix structure and its strength. Importantly, the bioremodelability of the tissue matrix is preserved in part by the cleaning process as it is free of bound detergent residues that would adversely affect the bioremodelability of the collagen. Additionally, the collagen molecules have retained their telopeptide regions as the tissue has not undergone treatment with enzymes during the cleaning process.

The collagen layers of the prosthetic device may be from the same collagen material, such as two or more layers of ICL, or from different collagen materials, such as one or more layers of ICL and one or more layers of fascia lata.

The processed tissue matrices may be treated or modified, either physically or chemically, prior to fabrication of a bioengineered graft prosthesis. Physical modifications such as shaping, conditioning by stretching and relaxing, or perforating the cleaned tissue matrices may be performed as well as chemical modifications such as binding growth factors, selected extracellular matrix components, genetic material, and other agents that would affect bioremodeling and repair of the body part being treated, repaired, or replaced.

As ICL is the most preferred starting material for the production of the bioengineered graft prostheses of the invention, the methods described below are the preferred methods for producing bioengineered graft prostheses comprising ICL.

In the most preferred embodiment, the tunica submucosa of porcine small intestine is used as a starting material for the bioengineered graft prosthesis of the invention. The small intestine of a pig is harvested, its attendant tissues removed and then mechanically cleaned using a gut cleaning machine which forcibly removes the fat, muscle and mucosal layers from the tunica submucosa using a combination of mechanical action and washing using water. The mechanical action can be described as a series of rollers that compress and strip away the successive layers from the tunica submucosa when the intact intestine is run between them. The tunica submucosa of the small intestine is comparatively harder and stiffer than the surrounding tissue, and the rollers squeeze the softer components from the submucosa. The result of the machine cleaning was such that the submucosal layer of the intestine solely remained.

After mechanical cleaning, a chemical cleaning treatment is employed to remove cell and matrix components, preferably performed under aseptic conditions at room temperature. The intestine is then cut lengthwise down the lumen and then cut into approximately 15 cm square sheet sections. Material is weighed and placed into containers at a ratio of about 100:1 v/v of solution to intestinal material. In the most preferred chemical cleaning treatment, such as the method disclosed in International PCT Application WO 98/49969, the disclosure of which is incorporated herein, the collagenous tissue is contacted with a chelating agent, such as ethylenediaminetetraacetic tetrasodium salt (EDTA) under alkaline conditions, preferably by addition of sodium hydroxide (NaOH): followed by contact with an acid where the acid contains a salt, preferably hydrochloric acid (HCl) containing sodium chloride (NaCl); followed by contact with a buffered salt solution such as 1 M sodium chloride (NaCl)/10 mM phosphate buffered saline (PBS): finally followed by a rinse step using water.

Each treatment step is preferably carried out using a rotating or shaking platform. After rinsing, the water is then removed from each container and the ICL is blotted of excess water using sterile absorbent towelettes. At this point, the ICL may be stored frozen at −80° C., at 4° C. in sterile phosphate buffer, or dry until use in fabrication of a prosthesis. If to be stored dry, the ICL sheets are flattened on a surface such as a flat plate, preferably a plate or membrane, such as a rigid polycarbonate sheet, and any lymphatic tags from the abluminal side of the material are removed using a scalpel, and the ICL sheets are allowed to dry in a laminar flow hood at ambient room temperature and humidity.

The ICL is a planar sheet structure that can be used to fabricate various types of constructs to be used as a prosthesis with the shape of the prosthesis ultimately depending on its intended use. To form prostheses of the invention, the constructs must be fabricated using a method that preserves the bioremodelability of the processed matrix material but also is able to maintain its strength and structural characteristics in its performance as a replacement tissue. The processed tissue matrix sheets are layered to contact another sheet or tubulated and wrapped over on itself. The area of contact is a bonding region where layers contact. The bonding region must be able to withstand suturing and stretching during implantation and in the initial healing phase until the patients cells populate and subsequently biomodel the prosthesis to form a new tissue. When used as a conduit or a duct, the bonding region must be able to withstand pressures of the matter it contains or is passing, particularly when used as a vascular graft under the systolic and diastolic pressures of systemic blood flow.

In a preferred embodiment, the prosthetic device of this invention is a tubular construct formed from a single, generally rectangular sheet of processed tissue matrix. The processed tissue matrix is rolled so that one edge meets and overlaps an opposing edge. The overlap serves as a bonding region. As used herein, "bonding region" means an area of contact between tow or more layers of the same or difference processed tissue matrix treated in a manner such that the layers are superimposed on each other and are sufficiently held together by self-lamination and chemical linking. For instance, a multilayer sheet construct of ICL is used to repair body wall structures such as a pericardial patch or a hernia repair device, tubular constructs can be used to repair tubular organs that serve as conduits such as vasculature or digestive tract structures or used as a neuron growth tube to guide nerve regeneration. They may also be implanted for tissue bulking and augmentation. A number of layers of ICL may be incorporated in the construct for bulking or strength indications. Prior implantation, the layers may be further treated or coated with collagen or other extracellular matrix components, hyaluronic acid, or heparin, growth factors, peptides or cultured cells.

In a preferred embodiment, an ICL sheet is formed into a tubular prosthesis. The ICL tube may be fabricated in various diameters, lengths, and number of layers and may incorporate other components depending on the indication for its use. The tubular ICL construct may be used as a vascular graft. For this indication, the graft comprises at least one layer with at least a 5% overlap to act as a bonding region that forms a tight seam and the luminal surface is preferably treated with heparin or an agent that prevents thrombosis. Other means for preventing thrombosis are known in the art of fabricating vascular constructs. In another vascular indication, the tubular ICL construct is formed on a metal stent to provide a cover for the stent. When implanted, the ICL benefits the recipient by providing a smooth protective covering for the stent, to prevent additional damage to host tissue during deployment. Tubular ICL prostheses may also be used to repair or replace other normally tubular structures such as gastrointestinal tract sections, urethra, ducts, etc. It may also be used in nervous system repair when fabricated into a nerve growth tube packed with extracellular matrix components, growth factors, or cultured cells.

In another preferred vascular indication, the tubular ICL construct may be used as an external stent in cases where damaged or diseased blood vessels or autograft vessels require exterior support. In one such indication, vein autografts are transplanted within the body and external support for the transplanted vein is desired. Before the transplanted vessel is fully anastomosed to the existing vasculature, the vessel is first passed through the lumen of an ICL tube. The vessel is then anastomosed and then the ends of the ICL tube are then secured to maintain the position of the construct.

To form a tubular construct, a mandrel is chosen with a diameter measurement that will determine the diameter of the formed construct. The mandrel is preferably cylindrical or oval in cross section and made of glass, stainless steel or of a nonreactive, medical grade composition. The mandrel may be straight, curved, angled, it may have branches or bifurcations, or a number of these qualities. The number of layers intended for the tubular construct to be formed corresponds with the number of times an ICL is wrapped around a mandrel and over itself. The number of times the ICL can be wrapped depends on the width of the processed ICL sheet. For a two layer tubular construct, the width of the sheet must be sufficient for wrapping the sheet around the mandrel at least twice. It is preferable that the width be sufficient to wrap the sheet around the mandrel the required number of times and an additional percentage more as an overlap to serve as a bonding region, for a single layer construct, preferably between about 5% to about 20% of the mandrel circumference to serve as a bonding region and to form a tight seam. Similarly, the length of the mandrel will dictate the length of the tube that can be formed on it. For ease in handling the construct on the mandrel, the mandrel should be longer than the length of the construct so the mandrel, and not the construct being formed, is contacted when handled.

The ICL has a sidedness quality derived from its native tubular state. The ICL has two opposing surfaces: a mucosal surface that faced the intestinal lumen and a serosal surface that previously had exterior intestinal tissues attached to it, such as mesentery and vasculature. It has been found that these surfaces have characteristics that can affect post-operative performance of the prosthesis but can be leveraged for enhanced device performance. In the formation of a tubular construct for use in as a vascular graft, it is preferred that the mucosal surface of the material be the luminal surface of the tubular graft when formed. In vascular applications, having the mucosal surface contact the blood flow provides an advantage as it has some nonthrombogenic properties that are preferred to prevent occlusion of the graft when it has been implanted in a patient. In other tubular constructs, the orientation of the layer of the construct depends on the intended use.

It is preferred that the mandrel is provided with a covering of a nonreactive, medical grade quality, elastic, rubber or latex material in the form of a sleeve. While a tubular ICL construct may be formed directly on the mandrel surface, the sleeve facilitates the removal of the formed tube from the mandrel and does not adhere to, react with, or leave residues on the ICL. To remove the formed construct, the sleeve may be pulled from one end off the mandrel to carry the construct from the mandrel with it. Because the processed ICL only lightly adheres to the sleeve and is more adherent to other ICL layers, fabricating ICL tubes is facilitated as the tubulated contract may be removed from the mandrel without stretching or otherwise stressing or risking damage to the construct. In the most preferred embodiment, the sleeve comprises KRATON® (Shell Chemical Company), a thermoplastic rubber composed of styrene-ethylene/butylene-styrene copolymers with a very stable saturated midblock.

For simplicity in illustration, a two-layer tubular construct with a 4 mm diameter and a 10% overlap is formed on a mandrel having about a 4 mm diameter. The mandrel is provided with a KRATON® sleeve approximately as long as the length of the mandrel and longer than the construct to he formed on it. A sheet of ICL is trimmed so that the width dimension is about 28 mm and the length dimension may vary depending on the desired length of the construct. In the sterile field of a laminar flow cabinet, the ICL is then formed into an ICL collagen tube by the following process. The ICL is moistened along one edge and is aligned with the sleeve-covered mandrel and, leveraging the adhesive nature of the ICL, it is "flagged" alone the length of the sleeve-covered mandrel and dried in position for at least 10 minutes or more. The flagged ICL is then hydrated and wrapped around the mandrel and then over itself one full revolution plus 10% of the circumference, for a 110% overlap, to serve as a bonding region and to provide a tight seam. To obtain a tubular construct with the mucosal side of the ICL as the lumen of the formed construct, the mucosal side of the ICL is moistened along one edge, flagged on the mandrel, and wrapped so that the mucosal isde of the ICL faces the mandrel.

For the formation of single layer tubular construct, the ICL must be able to wrap around the mandrel one full revolution and at least about a 5% of an additional revolution as an overlap to provide a bonding region that is equal to about 5% of the circumference of the construct. For a two-layer construct, the ICL must be able to wrap around the mandrel at least twice and preferably an additional 5% to 20% revolution as an overlap. While the two-layer wrap provides a bonding region of 100% between the ICL surfaces, the additional percentage for overlap ensures a tight, impermeable seam. For a three-layer construct, the ICL must be able to wrap around the mandrel at least three times and preferably an additional 5% to 20% revolution as an overlap. The construct may be prepared with any number of layers depending on the specifications for a graft required by the intended indication. Typically, a tubular construct will have 10 layers or less, preferably between 2 to 6 layers and more preferably 2 or 3 layers with varying degrees of overlap. After wrapping, any air bubbles, folds, and creases are smoothed out from under the material and between the layers.

ICL may be rolled either manually or with the assistance of an apparatus that aids for even tensioning and smoothing out air or water bubbles or creases that can occur under the mandrel or between the layers of ICL. The apparatus would have a surface that the mandrel can contact along its length as it is turned to wrap the ICL.

The layers of the wrapped ICL are then bonded together by dehydrating them while in wrapped arrangement on the sleeve-covered mandrel. While not wishing to be bound by theory, dehydration brings the extracellular matrix components, such as collagen fibers, in the layers together when water is removed from the spaces between the fibers in the matrix.

Dehydration may be performed in air, in a vacuum, or by chemical means such as by acetone or an alcohol such as ethyl alcohol or isopropyl alcohol. Dehydration may be done to room humidity, normally between about 10% Rh to about 20% Rh, or less, or about 10% to 20% moisture by weight. Dehydration may be easily performed by angling the mandrel with the ICL layers up into the oncoming airflow of the laminar flow cabinet for at least about 1 hour up to 24 hours at ambient room temperature, approximately 20° C., and at room humidity. At this point the wrapped dehydrated ICL constructs may be then pulled off the mandrel via the sleeve or left on for further processing. The constructs may be rehydrated in an aqueous solution, preferably water, by transferring them to a room temperature container containing rehydration agent for at least about 10 to about 15 minutes to rehydrate the layers without separating or delaminating them.

The constructs are then crosslinked together by contacting them with a crosslinking agent, preferably a chemical crosslinking agent that preserves the bioremodelability of the ICL material. As mentioned above, the dehydration brings the extracellular matrix components of adjacent ICL layers together for crosslinking those layers of the wrap together to form chemical bonds between the components and thus bond the layers together. Alternatively, the constructs may be rehydrated before crosslinking by contacting an aqueous solution, preferably water, by transferring them to a room temperature container containing rehydration agent for at least about 10 to about 15 minutes to rehydrate the layers without separating or delaminating them. Crosslinking the bonded prosthetic device also provides strength and durability to the device to improve handling properties. Various types of crosslinking agents are known in the art and can be used such as ribose and other sugars, oxidative agents and dehydrothermal (DHT) methods. A preferred crosslinking agent is 1-ethyl-3-(3-dimethylaminopropyl)carbodiimide hydrochloride (EDC). In another preferred method, sulfo-N-hydroxysuccinimide is added to the EDC crosslinking agent as described by Staros, J. V., *Biochem.* 21, 3950–3955, 1982. Besides chemical crosslinking agents, the layers may be bonded together by other means such as with fibrin-based glues or medical grade adhesives such as polyurethane, vinyl acetate or polyepoxy. In the most preferred method, EDC is solubilized in water at a concentration preferably between about 0.1 mM to about 100 mM, more preferably between about 1.0 mM to about 10 mM, most preferably at about 1.0 mM. Besides water, phosphate buffered saline or (2-[N-morpholino]ethanesulfonic acid) (MES) buffer may be used to dissolve the EDC. In addition, other agents may be added to the solution such as acetone or an alcohol may be added up to 99% v/v in water to make crosslinking more uniform and efficient. EDC crosslinking solution is prepared immediately before use as EDC will lose its activity over time. To contact the crosslinking agent to the ICL, the hydrated, bonded ICL constructs are transferred to a container such as a shallow pan and the crosslinking agent gently decanted to the pan ensuring that the ICL layers are both covered and free-floating and that no air bubbles are present under or within the layers of ICL constructs. The pan is covered and the layers of ICL are allowed to crosslink for between about 4 to about 24±2 hours after which time the crosslinking solution is decanted and disposed of.

Constructs are rinsed in the pan by contacting them with a rinse agent to remove residual crosslinking agent. A preferred rinse agent is water or other aqueous solution. Preferably, sufficient rinsing is achieved by contacting the chemically bonded constructs three times with equal volumes of sterile water for about five minutes for each rinse. If the constructs have not been removed from the mandrels, they may be removed at this point by pulling the sleeves from the mandrels. The constructs are then allowed to dry and when dry, the sleeve may be removed from the lumen of the constructs simply by pulling it out by one of the free ends.

In embodiments where the construct will be used as a vascular graft, the construct is rendered non-thrombogenic by applying heparin to the lumen of the formed tube. Heparin can be applied to the prosthesis, by a variety of well-known techniques. For illustration, heparin can be applied to the prosthesis in the following three ways. First, benzalkonium heparin (BA-Hep) isopropyl alcohol solution is applied to the prosthesis by vertically filling the lumen or dipping the prosthesis in the solution and then air-drying it. This procedure treats the collagen with an ionically bound BA-Hep complex. Second, EDC can be used to activate the heparin and then to covalently bond the heparin to the collagen fiber. Third, EDC can be used to activate the collagen, then covalently bond protamine to the collagen and then ionically bond heparin to the protamine. Many other coating, bonding, and attachment procedures are well known in the art which could also be used.

Constructs are then terminally sterilized using means known in the art of medical device sterilization. A preferred method for sterilization is by contacting the constructs with sterile 0.1% peracetic acid (PA) treatment neutralized with a sufficient amount of 10 N sodium hydroxide (NaOH), according to U.S. Pat. No. 5,460,962, the disclosure of which is incorporated herein. Decontamination is performed in a container on a shaker platform, such as 1 L Nalge containers, for about 18±2 hours. Constructs are then rinsed by contacting them with three volumes of sterile water for 10 minutes each rinse.

The constructs of the invention may also be sterilized using gamma irradiation. Constructs are packaged in containers made from material suitable for gamma irradiation and sealed using a vacuum sealer, which were in turn placed in hermetic bags for gamma irradiation between 25.0 and 35.0 kGy. Gamma irradiation significantly, but not detrimentally, decreases Young's modulus and shrink temperature. The mechanical properties after gamma irradiation are still sufficient for use in a range of applications and gamma is a preferred means for sterilizing as it is widely used in the field of implantable medical devices.

Tubular prostheses may be used, for example, to replace cross sections of tubular organs such as vasculature, esophagus, trachea, intestine, and fallopian tubes. These organs have a basic tubular shape with an outer surface and an inner luminal surface. Flat sheets may also be used for organ support, for example, to support prolapsed or hypermobile organs by using the sheet as a sling for the organs, such as bladder or uterus. In addition, flat sheets and tubular structures can be formed together to form a complex structure to replace or augment cardiac or venous valves.

The bioengineered graft prostheses of the invention may be used to repair or replace body structures that have been damaged or diseased in host tissue. While functioning as a substitute body part or support, the prosthesis also functions as a bioremodelable matrix scaffold for the ingrowth of host cells. "Bioremodeling" is used herein to mean the production of structural collagen, vascularization, and cell repopulation by the ingrowth of host cells at a rate about equal to the rate of biodegradation, reforming and replacement of the matrix components of the implanted prosthesis by host cells and enzymes. The graft prosthesis retains its structural characteristics while it is remodeled by the host into all, or substantially all, host tissue, and as such, is functional as an analog of the tissue it repairs or replaces.

The shrink temperature (° C.) of the tissue matrix prosthesis is an indicator of the extent of matrix crosslinking. The higher the shrink temperature, the more crosslinked the material. Non-crosslinked ICL has a shrink temperature of about 68±0.3° C. In the preferred embodiment, EDC crosslinked prostheses should have a shrink temperature between about 68±0.3° C. to about 75±1° C.

The mechanical properties include mechanical integrity such that the prosthesis resists creep during bioremodeling, and additionally is pliable and suturable. The term "pliable" means good handling properties for ease in use in the clinic.

The term "suturable" means that the mechanical properties of the layer include suture retention which permits needles and suture materials to pass through the prosthesis material at the time of suturing of the prosthesis to sections of native tissue, a process known as anastomosis. During suturing, such prostheses must not tear as a result of the tensile forces applied to them by the suture, nor should they tear when the suture is knotted. Suturability of prostheses, i.e., the ability of prostheses to resist tearing while being sutured, is related to the intrinsic mechanical strength of the prosthesis material, the thickness of the graft, the tension applied to the suture, and the rate at which the knot is pulled closed. Suture retention for a highly crosslinked flat 6 layer prosthesis crosslinked in 100 mM EDC and 50% acetone is at least about 6.5 N. Suture retention for a 2-layer tubular prosthesis crosslinked in 1 mM EDC in water is about 3.9 N±0.9 N. The preferred lower suture retention strength is about 2 N for a crosslinked flat 2 layer prosthesis; a surgeon's pull strength when suturing is about 1.8 N.

As used herein, the term "non-creeping" means that the biomechanical properties of the prosthesis impart durability so that the prosthesis is not stretched, distended, or expanded beyond normal limits after implantation. As is described below, total stretch of the implanted prosthesis of this invention is within acceptable limits. The prosthesis of this invention acquires a resistance to stretching as a function of post-implantation cellular bioremodeling by replacement of structural collagen by host cells at a faster rate than the loss of mechanical strength of the implanted materials due from biodegradation and remodeling.

The processed tissue material of the present invention is "semi-permeable," even though it has been layered and bonded. Semi-permeability permits the ingrowth of host cells for remodeling or for deposition of agents and components that would affect bioremodelability, cell ingrowth, adhesion prevention or promotion, or blood flow. The "non-porous" quality of the prosthesis prevents the passage of fluids intended to be retained by the implantation of the prosthesis. Conversely, pores may be formed in the prosthesis if a porous or perforated quality is required for an application of the prosthesis.

The mechanical integrity of the prosthesis of this invention is also in its ability to be draped or folded, as well as the ability to cut or trim the prosthesis obtaining a clean edge without delaminating or fraying the edges of the construct.

The following examples are provided to better explain the practice of the present invention and should not be interpreted in any way to limit the scope of the present invention. It will be appreciated that the device design in its composition, shape, and thickness is to be selected depending on the ultimate indication for the construct. Those skilled in the art will recognize that various modifications can be made to the methods described herein while not departing from the spirit and scope of the present invention.

EXAMPLES

Example 1

Chemical Cleaning of Mechanically Cleaned Porcine Small Intestine

The small intestine of a pig was harvested and mechanically stripped, using a Bitterling gut cleaning machine (Nottingham, UK) which forcibly removes the fat, muscle and mucosal layers from the tunica submucosa using a combination of mechanical action and washing using water. The mechanical action can be described as a series of rollers that compress and strip away the successive layers from the tunica submucosa when the intact intestine is run between them. The tunica submucosa of the small intestine is comparatively harder and stiffer than the surrounding tissue, and the rollers squeeze the softer components from the submucosa. The result of the machine cleaning was such that the submucosal layer of the intestine solely remained. The remainder of the procedure was performed under aseptic conditions and at room temperature. The chemical solutions were all used at room temperature. The intestine was then cut lengthwise down the lumen and then cut into 15 cm sections. Material was weighed and placed into containers at a ratio of about 100:1 v/v of solution to intestinal material.

A. To each container containing intestine was added approximately 1 L solution of 0.22 μm (micron) filter sterilized 100 mM ethylenediaminetetraacetic tetrasodium salt (EDTA)/10 mM sodium hydroxide (NaOH) solution. Containers were then placed on a shaker table for about 18 hours at about 200 rpm. After shaking, the EDTA/NaOH solution was removed from each bottle.

B. To each container was then added approximately 1 L solution of 0.22 μm filter sterilized 1 M hydrochloric acid (HCl)/1 M sodium chloride (NaCl) solution. Containers were then placed on a shaker table for between about 6 to 8 hours at about 200 rpm. After shaking, the HCl/NaCl solution was removed from each container.

C. To each container was then added approximately 1 L solution of 0.22 μm filter sterilized 1 M sodium chloride (NaCl)/10 mM phosphate buffered saline (PBS). Containers were then placed on a shaker table for approximately 18 hours at 200 rpm. After shaking, the NaCl/PBS solution was removed from each container.

D. To each container was then added approximately 1 L solution of 0.22 μm filter sterilized 10 mM PBS. Containers were then placed on a shaker table for about two hours at 200 rpm. After shaking, the phosphate buffered saline was then removed from each container.

E. Finally, to each container was then added approximately 1 L of 0.22 μm filter sterilized water. Containers were then placed on a shaker table for about one hour at 200 rpm. After shaking, the water was then removed from each container.

Processed ICL samples were cut and fixed for histological analyses. Hemotoxylin and eosin (H&E) and Masson trichrome staining was performed on both cross-section and long-section samples of both control and treated tissues. Processed ICL samples appeared free of cells and cellular debris while untreated control samples appeared normally and expectedly very cellular.

Example 2

Comparative Study of Other Cleaning Treatments for Collagenous Tissue

Other methods for disinfecting and sterilizing collagenous tissues described in U.S. Pat. No. 5,460,962 to Kemp were compared to similar methods described by Cook. et al. in International PCT application WO 98/22158. Examples 1, 2, and 3, from Kemp, in addition to a non-buffered peracetic acid method were done.

Small intestines were harvested from 4 large pigs. Intestines were procured, the outer mesenteric layer was stripped, and the intestines were flushed with water.

The study included seven conditions: Condition A was carried out according to the disclosure of Example 1 in Cook, et al. in International PCT Application WO 98/22158. Condition B was a variation of A in that the intestinal material was mechanically cleaned before employing the disclosed chemical treatment. Conditions C, D, and E were carried out according to the methods of Examples 1, 2, and 3 in U.S. Pat. No. 5,460,962 to Kemp. In all conditions, a ten-to-one ratio of solution to material is used, that is, 100 g of tissue material is treated with 1 L of solution.

A. Material from each of the 4 intestines were placed into separate bottles (n=5) containing a one liter solution of 0.2% peracetic acid in 5% ethanol (pH 2.56) and agitated on a shaker platform. After two hours of agitation, condition A was mechanically cleaned on the Bitterling gut cleaning machine.

For the other six conditions, B through G, intestine was mechanically cleaned using the Bitterling gut cleaning machine prior to chemical treatment. After mechanical cleaning, representative pieces from the 4 intestines were placed into bottles containing solution for chemical treatment. Bottles were shaken 18±2 hours on a platform. The remaining six conditions, B through G, were as follows:

B. A one liter solution of 0.2% peracetic acid in 5% ethanol (pH 2.56) (n=5).

C. A one liter solution of 0.1% peracetic acid in phosphate buffered saline (pH 7.2) (n=3).

D. A one liter solution of 0.1% peracetic acid and 1M sodium chloride (NaCl) (pH 7.2) (n=3).

E. A one liter solution of 0.1% peracetic acid and 1M NaCl (pH 2.9) (n=3).

F. One liter solution of "chemical cleaning" solutions as mentioned above in Example 1 (n=4).

G. A one liter solution of 0.1% peracetic acid in deionized water, buffered to pH 7.0 (n=2).

After chemical and mechanical treatments, all conditions were rinsed for a total of 4 times with filtered sterile purified water. The mechanically and chemically treated material was grossly stained to examine cellular debris with Mayer's hematoxylin. Morphological assessment included Hematoxylin & Eosin, Masson's Trichrome, and Alizarin Red staining techniques. Histological results from the various treatments show that the method of condition A yielded a material where it was difficult to remove mucosal layers on Bitterling after chemical treatment. The material had to be run through Bitterling about an extra 10–12 times. The material was very swollen at first and had a significantly large amount of cellular debris on surface and in the vasculature of the material. The method of condition B was also very swollen and also demonstrated a significantly large amount of cellular debris on surface and in the vasculature of the material. The methods of conditions C and D yielded a non-swollen material having minimal cellular debris in vasculature. Condition E yielded a material that was slightly swollen and contained minimal cellular debris in the vasculature.

A DNA/RNA isolation kit (Amersham Life Sciences) was used to quantify the residual DNA/RNA contained in the cleaned tissues. The results are summarized in Table 1.

TABLE 1

| | DNA/RNA Isolation kit Results ($\mu$g DNA/mg tissue) | | | | | | |
|---|---|---|---|---|---|---|---|
| Condition | A | B | C | D | E | F | G |
| Average ± Std. Dev. | 2.16 ± 0.32 | 2.1 ± 0.48 | 0.32 ± 0.11 | 1.92 ± 0.28 | 0.32 ± 0.23 | 0 ± 0 | 1.42 ± 0.03 |

Morphological analysis correlates with the DNA/RNA quantification to show that the cleaning regimens of conditions A and B result in a collagenous tissue matrix that remains highly cellular and contain residual DNA as a result. The cleaning methods of Kemp are much more effective for the removal of cells and cellular debris from collagenous tissue matrices. Finally, the chemical cleaning method of Condition F, described in International PCT Application No. WO 98/49969 to Abraham, et al. and outlined in Example 1, above, removes all cells and cellular debris and their DNA/RNA to a level undetectable by these methods.

Example 3

Method for Making an ICL Tube Construct

In the sterile field of a laminar flow cabinet, the ICL was formed into ICL collagen tubes by the following process. Lymphatic tags were trimmed from the serosal surface of the ICL. The ICL was blotted with sterile absorbent towelettes to absorb excess water from the material and then spread on a porous polycarbonate sheet and dried in the oncoming airflow of the laminar flow cabinet. Once dry, ICL was cut into 28.5 mm×10 cm pieces for a 2 layer graft with approximately a 10% overlap. To support the ICL in the formation of the tubes, a cylindrical stainless steel mandrel with a diameter of about 4 mm was covered with KRATON®, an elastic sleeve material that facilitates the removal of the formed collagen tube from the mandrel and does not adhere or react with the ICL. The lone edge of the ICL was then moistened with sterile water and adhered to the mandrel and allowed to dry for about 15 minutes to form a "flag". Once adhered, the ICL was rolled around the mandrel and over itself one complete revolution. After rolling was complete, air bubbles, folds, and creases were smoothed out from under the material and between the layers. The mandrels and rolled constructs were allowed to dry in the oncoming airflow of the laminar flow cabinet for about an hour in the cabinet at room temperature, approximately 20° C.

Chemical crosslinking solution of either crosslinked 1 mM EDC or 10 mM EDC/25% acetone v/v in water, in volumes of about 50 mL crosslinking solution per tube, was prepared immediately before crosslinking; EDC will lose its activity over time. The hydrated ICL tubes were then transferred to either of two cylindrical vessels containing either crosslinking agent. The vessel was covered and allowed to sit for about 18±2 hours in a fume hood, after which time the crosslinking solution was decanted and disposed. ICL tubes were then rinsed three times with sterile water for about 5 minutes per rinse.

The crosslinked ICL tubes were then removed from the mandrel by pulling the Kraton sleeve off the mandrel from one end. Once removed, the ICL tube containing the Kraton were allowed to dry for an hour in the hood. Once dried, the sleeve was removed from the lumen of the ICL tube simply by pulling it out from one end.

ICL tubes were sterilized in 0.1% peracetic acid at approximately pH 7.0 overnight according to the methods described in commonly owned U.S. Pat. No. 5,460,962, the disclosure of which is incorporated herein in its entirety. The ICL tubes were then rinsed of sterilization solution three times with sterile water for about 5 minutes per rinse. The peracetic acid sterilized ICL collagen tubes were then dried in the laminar flow hood and then packaged in sterile 15 mL conical tubes until implantation.

Example 4

Mechanical Testing of ICL Tube Prostheses

Various mechanical properties of a 2 layer ICL tubular construct formed from a single sheet of ICL wrapped around a mandrel with 20% overlap, crosslinked at 1 mM EDC in water was measured. Suture retention, burst. porosity (leakage/integral water permeability), and compliance testing were done in accordance with the "Guidance for the Preparation of Research and Marketing Applications for Vascular Graft Prostheses", FDA Draft Document, August 1993. Suture retention, burst and compliance analyses were performed using a servohydraullic MTS testing system with TestStar-SX software. Results are summarized in Table 2.

Briefly, the suture retention test consisted of a suture being pulled 2.0 mm from the edge of a graft at a constant rate. The peak force when the suture ripped through the graft was measured. The average measurement obtained was above required limits indicating that the construct can withstand the physical pressures of suturing in the clinic.

In the burst test, pressure was applied to the graft in 2.0 psi increments for one minute intervals until the graft burst. For reference, systolic pressure is approximately 120 mmHg (16.0 kPa) in a normotensive person, thus the burst strength obtained by the testing demonstrated that the construct could maintain pressures about 7.75 times systolic pressure thus indicating that the construct can be grafted for vascular indications and withstand the rigors blood circulation.

For compliance testing, the graft was brought to 80 and 120 mmHg in succession. The diameter of the graft was then measured at each pressure using image analysis software and the compliance calculated as $(D_{120}-D_{80})/(D_{80} \times 40 \text{ mmHg}) \times 100\%$. Compliance of a rabbit carotid artery is approximately 0.07%/mmHg, human artery is about 0.06%/mmHg and human vein is about 0.02%/mmHg, indicating that the construct exhibits the requisite compliance to serve as a vascular graft.

To measure porosity, PBS under hydrostatic pressure of 120 mmHg is applied to the graft. The volume of PBS that permeated through the graft over a 72 hour period was normalized to the time and surface area of the graft to calculate the porosity.

The shrink temperature is used to monitor the extent of crosslinking in a collagenous material. The more crosslinked a graft, the more energy is required, thus a higher shrink temperature. A differential scanning calorimeter was used to measure the heat flow to and from a sample under thermally controlled conditions. The shrink temperature was defined as the onset temperature of the denaturation peak in the temperature-energy plot.

The suture retention is well above the 2 N suggested for suturing a prosthesis in a patient: a surgeon's pull force when suturing is about 1.8 N. The burst strength over seven times systolic pressure. The compliance is in the range of human arteries and veins. The porosity of the ICL tube is low compared to a woven graft: the ICL tube does not require pre-clotting. The shrink temperature, a measure of the collagen denaturation temperature, is close to that of non cross-linked ICL indicating a low amount of cross-linking. Mechanical testing was performed on the ICL sleeve prosthesis to determine the strength of the ICL sleeve. A summary of results from the various tests of mechanical and physical characteristics of 2-layer ICL constructs are presented in Table 2.

TABLE 2

Summary of Mechanical Properties

| Mechanical Test | Result |
| --- | --- |
| Suture Retention Test | 3.97 ± 0.7 N |
| Burst Test | 18.0 ± 5.4 psi (124 ± 37 kPa) |
| Porosity | $3.4 \times 10^{-4}$ ml/cm$^2$/min |
| Shrink Temperature | 68.4 ± 0.4° C. |
| Compliance (between 80 and 120 mmHg) | 0.05%/mmHg |

Example 5

Implantation of Collagen Tubes as External Stents

Twenty-nine New Zealand male white rabbits underwent interposition bypass grafting of the right common carotid artery using the reversed ipsilateral jugular vein. In the experimental group (n=15), once the proximal anastomosis was performed, the vein was passed through a collagen tube having dimensions of 4 mm in diameter and 35 to 40 mm in length and the distal anastomosis was then completed. Leaks were repaired and the collagen tube was fashioned to completely cover the vein graft, including both anastomoses. Control animals (n=14) were treated identically but without tube support. One intraoperative death resulted from an unrecognized leak in the mid-segment of a vein graft in the experimental group. Otherwise, there were no other significant complications such as infection or bleeding in either group. All animals survived until end-points and all vein grafts were patent at harvest. Postoperatively, the flow rate and intraluminal pressure in vein grafts were measured on either day 3 or 28 (n=5 per group). Vein grafts were harvested on day 3 for assessment of tyrosine phosphorylation by Western blot analysis (n=4 per group), and on day 28 for morphometric measurement (n=5 per group), scanning and transmission electron microscopy (n=5 per group) and isometric tension studies (n=5 per group). On the day of harvest, animals were anesthetized and subsequently sacrificed with an intravenous overdose of barbiturates.

Vein grafts implanted in the arterial circulation predictably develop wall thickening, with smooth muscle cell hyperplasia and deposition of extracellular matrix in the intima and media, an adaptive process that has been referred to as "arterialization". In 50% of implanted vein grafts, however, this process becomes pathologic usually due to intimal hyperplastic lesions causing either focal stenosis or promoting accelerated atherosclerosis. This study shows that external tube support of vein grafts effectively modulates tyrosine kinase signaling and the hyperplastic response in experimental vein grafts, with increased shear stress and reduced wall tension.

Example 6

Hemodynamic Assessment

The rate of blood flow was measured by applying flow probes (3 or 4 mm diameter), connected to flowmeter (Transonic Systems Inc., Ithaca, N.Y.), onto the external surface of the vessels; flow was measured with the collagen tube in situ in tube-supported vein grafts. The intraluminal blood pressure was measured using a 27-gauge needle, connected to a pressure transducer and monitor (Propaq 106, Protocol Systems Inc., Beaverton, Oreg.). Flow rates and intraluminal pressures were determined in the carotid artery (proximal and distal to the vein graft) and in the vein graft in a pilot study; there was no significant differences in the flow rates or pressure levels in vein grafts compared to the proximal or distal segments of carotid arteries. Hence, values reported for flow rate (Q; in ml·min$^{-1}$) were taken from the mid-segments of vein grafts and values for intraluminal blood pressure (P; in mmHg) from the proximal segments of the carotid arteries.

Shear stress was calculated as $\tau = 4\eta Q/\pi r_i^3$ in dyne/cm$^2$ ($\tau$, shear stress; $\eta$, blood viscosity; Q, flow rate; $r_i$, internal radius). Wall tension was calculated as $T=P \cdot r_i$ in $10^3$ dyne/cm$^1$ (T, wall tension; P, mean arterial blood pressure; $r_i$, internal radius). The blood viscosity (0.03 in poise) was assumed to be constant. The internal radius ($r_i$) was determined by morphometry; we previously demonstrated that histologic diameter underestimated the in situ diameter by 10%. For analytical purposes, the internal radii and wall tensions were recognized as approximations and the flow of blood was assumed to be laminar. To normalize the wall tension by wall thickness, the wall tensile stress was also calculated (wall tensile stress=pressure×internal radius/wall thickness). Wall thickness was defined as the sum of the thickness of the intima, the media, and the collagen tube, respectively.

Flow rates and pressures were not significantly altered in vein grafts with tube support as compared to controls (Table 3). Applying the equations formulated in above, the calculated wall tension was decreased by 1.7-fold and shear stress was increased by 4.8-fold in tube supported vein grafts compared to controls (Table 3). The decrease in wall tension was expected because the pressure was not different but the internal radius was reduced by 1.7-fold in tube supported vein grafts compared to controls (1.63±0.06 mm vs. 2.69±0.09 mm, respectively; p<0.0001). Similarly, the increase in shear stress was anticipated since flow was not significantly changed and shear stress is inversely proportional to the third power of the internal radius.

Hemodynamic forces are known to play an important role in the regulation of cells that compose the blood vessel wall. In particular, the effects of shear stress on endothelial cells have been studied extensively in vitro. Several shear stress-inducible endothelial genes have been identified in vitro, including PDGF-A, PDGF-B, basic fibroblast growth factor (FGF) and nitric oxide synthase, all of which have been implicated in wound remodeling. The transformation of biomechanical (hemodynamic) stimuli into biological responses usually begins with the activation of protein kinases and protein-to-protein interactions leading to gene transcription (or inhibition thereof). Takahashi and Berk, J Clin Invest. 34: 212–219 (1996), have demonstrated that shear stress can activate extracellular signal-regulated kinase (ERK½) via a tyrosine kinase-dependent pathway in cultured human umbilical vein endothelial cells. The hemodynamic factors in vivo are complex, however, the relative importance of each of these factors has been identified in animal models.

TABLE 3

Hemodynamic Parameters.

| | Tube Support | Control | p-value |
|---|---|---|---|
| Flow (ml · min$^{-1}$) | 12.8 ± 1.1 | 11.5 ± 1.0 | 0.41 |
| Pressure (mmHg) | 53.2 ± 3.8 | 57.8 ± 1.4 | 0.29 |
| Wall Tension (×10$^3$ dyne · cm$^{-1}$) | 11.7 ± 0.9 | 19.8 ± 0.5 | <0.01 |
| Shear Stress (dyne · cm$^{-2}$) | 1.9 ± 0.25 | 0.4 ± 0.04 | <0.001 |

Example 7

Protein Extraction and Western Blot Analysis

Excised vein grafts were cleared of adventitial tissues, washed in ice cold phosphate buffered saline (PBS), cut into 1 cm rings, snap frozen in liquid nitrogen and stored at −80° C. Proteins were extracted from the frozen samples by grinding the tissues to a fine powder in a mortar and pestle in liquid nitrogen followed by sonication in ice-cold lysis buffer (1:4 w:v; 50 mM Tris-HCl, pH 7.4, 1% NP-40, 0.25% sodium deoxycholate, 150 mM NaCl, 1 mM EGTA, 1 mM PMSF, 1 mM sodium orthovanadate, 1 mM sodium fluoride, 1 µg·ml$^{-1}$ aprotinin, 1 µg·ml$^{-1}$ leupeptin, and 1 µg·ml$^{-1}$ pepstatin). Insoluble debris was pelleted in a microcentrifuge at 14,000 g at 4° C. The supernatant was collected as cell lysates and stored at −80° C. until used. Protein concentration was determined using Bradford assay (Biorad Laboratories, Richmond, Calif.) with bovine serum albumin (BSA) as the standard.

Equal amounts of protein extracts (15 µg) were mixed in a gel loading buffer (20% glycerol, 100 mM Tris-HCl -pH 7.4, 100 mM NaCl, 100 mM dithiothreitol) (1:4; v/v) and boiled for 9 minutes. Samples were then loaded onto an 8% SDS-polyacrylamide minigel, separated by electrophoresis and transferred onto a nitrocellulose membrane. Nonspecific binding was blocked by incubating the membrane in TTBS (10 mM Tris-HCl, pH 8.0, 0.05% TWEEN-20 and 150 mM NaCl) containing 1% BSA overnight at 4° C. A monoclonal mouse anti-phosphotyrosine antibody (PY20, 1 µg/ml; Chemicon International Inc., Temecula, Calif.) was then applied to the blot for 1 hour at room temperature. Antibody binding was detected by incubating the blot with a horseradish peroxidase conjugated goat anti-mouse IgG (1:5000 dilution; Santa Cruz Biotechnology, Santa Cruz, Calif.). The blot was washed several times between blocking steps with TABS. The immunoblot was visualized using an enhanced chemiluminescence kit (Amersham, Arlington Heights, Ill.) and autoradiographed. The autoradiographs were scanned, analyzed (Adobe Photoshop 3.0, Adobe Systems Inc., Mountain View, Calif.) and the integrated density of visualized bands was measured (N.I.H Image 1.61). Chemicals were obtained from Sigma Chemical Co. (St Louis, Mo.) unless otherwise stated.

Western blot analysis demonstrated a 15-fold reduction (p<0.001) in phosphorylated tyrosine residues in the wall extracts of day 3 tube supported vein grafts, when compared to controls. Phosphorylated tyrosine residues were detected in approximately 113 kDa proteins in tube supported vein grafts. In control vein grafts, however, in addition to the greater amount of phosphorylated tyrosine residues in approximately 113 kDa proteins, phosphorylated tyrosine residues were also present in proteins with molecular weights just above 82 kDa and of 200 kDa Protein tyrosine kinase activity is markedly reduced in vein grafts with reduced wall tension and increased shear stress, both of which are the consequences of the tube support. The identity of the tyrosine phosphorylated proteins (of approximately 82, 113 and 200 kDa) remains to be further defied. However, we postulate that the decreased tyrosine kinase activity in tube supported vein grafts may, in part, be associated with reduced expression or activation of the receptors for growth factors, such as PDGF, FGF and epidermal growth factor; the receptors for these growth factors have intrinsic protein tyrosine kinases, which range from 110 to 170 kDa in molecular weight. Moreover, Kraiss et al. (Circ Res 1996;79:45–53) have shown that abrupt reduction in both blood flow and shear stress is associated with increased PDGF-A mRNA and protein expression in baboon prosthetic grafts.

In parallel, Mehta et al. (Nature Medicine 1998;4:235–239) have recently demonstrated a significant decrease in PDGF-B protein with external stenting of vein grafts in the pig model. Although wall tension and shear stress were not assessed in the study of Mehta et al, supra, their external stent model likely produced hemodynamic effects similar to our tube support model, that is, reduced wall tension and increased shear stress.

Example 8

Morphologic Assessment

Vein grafts were cleared of blood with an initial infusion of Hanks Balanced Salt Solution (Gibco Laboratories, Life Technologies Inc., Grand Island, N.Y.). As previously described, vein grafts were then perfused fixed in situ with 2% glutaraldehyde made up in 0.1M cacodylate buffer (pH 7.2) supplemented with 0.1M sucrose to give an osmolality of approximately 300 mOsm, at a pressure of 80 mmHg. After immersion in the fixative for 48 hours, cross-sections (3 per graft) from the middle segment of the vein grafts were processed for morphometric assessment. Briefly, morphometric assessment was performed on sections that were stained with a modified Masson's trichrome and Verhoeff's elastin stain. The intima and media were delineated by identification of the demarcation between the criss-cross orientation of the intimal hyperplastic smooth muscle cells and circular smooth muscle cells of the media. The outer limit of the media was defined by the interface between the circular smooth muscle cells of the media and the connective tissue of the adventitia. The dimensions of the lumen, intima and media were measured by videomorphometry (Innovision 150, American Innovision Inc., San Diego, Calif.). The internal radius and the thickness of the intima and media of vein grafts were derived from the measured luminal, intimal and medial areas. The intimal ratio (intimal ratio=intimal area/[intimal+medial areas]) and luminal index (luminal index=luminal diameter/[intimal+medial thicknesses]) were also calculated.

After further specimen processing as previously described, scanning electron microscopy (Philips 500 scanning electron microscope, N.V. Philips, Eindhoven, The Netherlands) and transmission electron microscopy (Philips 300 transmission electron microscope, N.V. Philips, Eindhoven, The Netherlands) were performed on representative mid-sections.

Externally supporting vein grafts with the collagen tube reduced the luminal diameter of day 28 vein grafts by 63% compared to control vein grafts (Table 4). The thickness of the intima was decreased by 45% (46±2 $\mu$m vs 84+5 $\mu$m, p<0.0001) and the media by 20% (63±8 $\mu$m vs 79±4 $\mu$m, p<0.05) in tube supported vein grafts compared to controls, respectively. Both intimal and medial areas were also reduced, 66% and 49%, respectively (Table 4). Due the greater reduction in intimal dimension relative to the reduction in the media, the intimal ratio was decreased by 10% (Table 4). However, the luminal index, an assessment of cross-sectional wall thickness relative to luminal diameter, was maintained constant with or without tube support (Table 4).

Scanning electron microscopy showed a confluent endothelial lining with distinct cell borders in both tube supported vein grafts and control vein grafts. Endothelial cells were unaltered and flattened in tube supported vein grafts compared to more cuboidal and bulging endothelial cells in the control vein graft. On transmission electron microscopy, vein grafts with tube support had less subendothelial edema and less debris than controls; additionally, the orientation of intimal smooth muscle cells were orderly and circular, and their shape was elongated and organized in several layers in tube supported vein grafts. In contrast, intimal smooth muscle cells were disorganized and less elongated in control vein grafts.

A multitude of hemodynamic factors are known to influence wall thickening in vein grafts. Schwartz, et al (J Vasc Surg 1992;15:176–186) have shown that "myointimal" (referring to both intima and media) thickening correlates most strongly with wall tension in rabbit vein grafts. On the other hand, Dobrin (Hypertension 1995;26:38–43) has demonstrated that intimal thickening correlates best with low flow velocity (a determinant of shear stress) and that medial thickening was a better correlate of deformation in the circumferential direction (a determinant of wall tension). The prevailing concept is that wall remodeling is dependent on both shear stress and wall tension. In this study, we found a greater reduction in intimal thickening than medial thickening which may correlate with the larger increase in shear stress and smaller decrease in wall tension, respectively, which would support Dobrin's results. Although wall thickening is due to both hyperplasia of smooth muscle cells and elaboration of an extracellular matrix, more is known about the former than latter. Zwolak, et al. (J Vasc Surg 1987;5:126–136) have described the cellular kinetics in the rabbit vein grafts. The proliferation of smooth muscle cells has been shown to increase in grafts subjected to low flow and shear stress. Additionally, Mehta, et al, supra, have reported that stenting of vein grafts reduces intimal and medial smooth muscle cell proliferation as assessed by immunostaining for the proliferating cell nuclear antigen (PCNA).

TABLE 4

Dimensional Analysis of Day 28 Vein Grafts.

| | Tube Support | Control | p-value |
|---|---|---|---|
| Luminal area (mm$^2$) | 8.6 ± 0.6 | 23.2 ± 1.6 | <0.001 |
| Intimal area (mm$^2$) | 0.48 ± 0.02 | 1.42 ± 0.08 | <0.001 |
| Medial area (mm$^2$) | 0.70 ± 0.11 | 1.36 ± 0.07 | <0.001 |
| Intimal ratio | 0.46 ± 0.06 | 0.51 ± 0.01 | <0.01 |
| Luminal index | 34.1 ± 3.6 | 34.9 ± 2.2 | 0.33 |

Intimal ratio = intimal area/(intimal + medial areas); luminal index = luminal diameter/(intimal + medial thickness). Values are the mean ± s.e.m (n = 5 per group).

Statistical differences between tube supported vein grafts and control vein grafts were compared using unpaired Mann-Whitney Rank sum test.

Example 9

Isometric Tension Studies

Vein grafts were sectioned into four 5 mm rings. In the tube supported group, the collagen tube was carefully dissected off and removed to allow unimpeded vessel contraction and relaxation. Each ring was immediately mounted between two stainless steel hooks in 5 ml organ baths containing oxygenated Krebs solution (122 mM NaCl, 4.7 mM KCl, 1.2 mM MgCl$_2$, 2.5 mM CaCl$_2$, 15.4 mM NaHCO$_3$, 1.2 mM KH$_2$PO$_4$ and 5.5 mM glucose, maintained at 37° C. and oxygenated with 95% O$_2$ and 5% CO$_2$), as previously described with some modifications. In brief, following equilibration, the resting tension was adjusted in increments from 0.5 to 1.25 gms and the maximal response to a modified oxygenated Krebs solution containing 60 mM KCl, 66.7 mM NaCl, 1.2 mM MgCl$_2$, 2.5 mM CaCl$_2$, 15.4 mM NaHCO$_3$, 1.2 mM KH$_2$PO$_4$ and 5.5 mM glucose was measured to establish a length-tension relationship. Cumulative dose response curves to the contractile agonists bradykinin ($10^{-9}$ to $10^{-4}$ M), norepinephrine ($10^{-9}$ to $10^{-4}$ M), and serotonin ($10^{-9}$ to $10^{-4}$ M) were performed. Relaxation responses to acetylcholine ($10^{-8}$ to $10^{-4}$ M), an endothelium dependent agonist, and nitroprusside ($10^{-8}$ s to $10^{-4}$ M), an endothelium independent agonist, were assessed on rings precontracted with norepinephrine, at the concentration which produced 80% of maximal contraction. All rings were allowed to re-equilibrate for a minimum of 30 minutes between each experimental run and the same sequence of agonist testing was maintained for all experiments. (All chemicals were obtained from Sigma Chemical Co. (St Louis, Mo.)).

Tube supported vein grafts demonstrated similar responses to KCl compared to controls (force: 300±46 mg vs 280±47 mg). The sensitivities of tube supported vein grafts in response to norepinehrine and serotonin were not significantly different than that of controls (Table 5). Tube supported vein grafts were, however, more sensitive to bradykinin than controls (Table 5). The maximal contractile forces generated in response to all three agonists (norepinephrine, serotonin and bradykinin), expressed as standardized contractile ratios, were not significantly altered with external tube support of vein grafts.

As previously reported, control vein grafts did not relax in response to acetylcholine. In contrast, 10 of 20 rings from tube supported vein grafts demonstrated dose-dependent relaxation in response to acetylcholine with a maximal relaxation to 64% of precontracted tension, albeit with a low sensitivity (Table 5). Of the five tube supported vein grafts studied, only one had no response to acetylcholine in all rings. In response to nitroprusside, the sensitivity (Table 5) and maximal relaxation were similar in vein grafts with or without tube support.

These results show complete preservation of smooth muscle cell function and recovery of endothelial-dependent relaxation with tube support of vein grafts. Despite the significant reduction in wall thickness, tube supported vein grafts generated similar contractile forces in response to KCl and all three contractile agonists tested (norepinephrine, serotonin and bradykinin). The maximal force generated by a vessel ring can be correlated with smooth muscle cell mass, provided that all other factors (such as the integrity and number of receptors for the agonist or potassium channels) are constant. It would follow that smooth muscle cell mass was not significantly changed with tube support, suggesting that the reduction in intimal thickness may in part be due to decreased production of extracellular matrix.

TABLE 5

Vasomotor Responses of Day 28 Vein Grafts.

| | Tube Support | Control | p-value |
|---|---|---|---|
| Norepinephrine | 5.96 ± 0.07 | 5.97 ± 0.06 | 0.91 |
| Serotonin | 6.39 ± 0.11 | 6.28 ± 0.07 | 0.22 |
| Bradykinin | 6.32 ± 0.08 | 5.60 ± 0.09 | <0.001 |
| Acetylcholine | 3.92 ± 0.22 | no response | <0.01 |
| Nitroprusside | 6.46 ± 0.12 | 6.73 ± 0.19 | 0.25 |

The concentration for the half maximal response (EC$_{50}$) was csalculated by logistic analysis and the sensitivity is defined as $-\log_{10}(EC_{50})$. In each vein graft, the sensitivity was determined for each vessel ring (4 rings per vein graft) and the mean was taken as the value for that vein graft. Values shown are the mean±s.e.m (n=5 per group). Statistical differences between the tube supported vein grafts and control vein grafts were compared using the unpaired Student's t-test.

The recovery of endothelium-dependent relaxation to acetylcholine in 50% of vessel rings with tube support would indicate that endothelial function was modulated. Increased shear stress has been shown to stimulate increased production of nitric oxide in vitro, which may explain in part the relaxation to acetylcholine in tube supported vein grafts. Systemic supplementation with L-arginine, the nitric oxide precursor, has also been shown to preserve endothelial-dependent relaxation of vein grafts to acetylcholine. Improved endothelial function has also been reported by Onohara, et al (J Surg Res 1993:55:344–350) with increased prostacyclin (PGI) production in vein grafts exposed to high shear stress. Alternatively, the preserved endothelial function in vein grafts may be attributed to the lesser wall stretch injury with tube support. All in all, endothelial cells are known to have regulatory role in smooth muscle cell proliferation and migration in addition to its role in mechanotransduction and vasomotor responses. We therefore postulate that improved endothelial function with tube support may reduce the release of mitogenic and chemoattractant signals such as PDGF.

Although the foregoing invention has been described in some detail by way of illustration and example for purposes of clarity and understanding, it will be obvious to one of skill in the art that certain changes and modifications may be practiced within the scope of the appended claims.

We claim:

1. A method for producing a collagen tube comprising at least one layer of submucosal collagen of small intestine wherein the method comprises:

(a) rolling the submucosal collagen around a mandrel and over itself one complete revolution to form a two layer submucosal collagen tube;
(b) drying the tube on the mandrel;
(c) contacting the tube with a crosslinking agent to crosslink the collagen;
(d) removing the crosslinking agent by rinsing the tube;
(e) drying the crosslinked tube on the mandrel; and,
(f) removing the tube from the mandrel.

2. The method of claim 1 further comprising the step
(g) contacting the collagen tube with a peracetic acid to sterilize the collagen tube.

3. A method of using a bioremodelable prosthesis comprising a collagen tube comprising at least one layer of processed tissue matrix of crosslinked submucosal collagen to prevent stretch injury in an autologous vein graft having two ends implanted in the arterial circulation comprising:
(a) removing a segment of vasculature;
(b) anastomosizing a first end of the vein graft;
(c) passing the vein graft through a collagen tube;
(d) anastomosizing a second end of the vein graft; and,
(e) covering the vein graft and both anastomoses with said collagen tube.

* * * * *

UNITED STATES PATENT AND TRADEMARK OFFICE
CERTIFICATE OF CORRECTION

PATENT NO.      : 6,572,650 B1                                                            Page 1 of 1
DATED           : June 3, 2003
INVENTOR(S)     : Abraham et al.

It is certified that error appears in the above-identified patent and that said Letters Patent is hereby corrected as shown below:

<u>Title page,</u>
Item [75], Inventors, should read:

-- [75] Inventors: Ginger A. Abraham, Braintree, MA (US); Robert M. Carr, Jr., West Roxbury, MA (US); Tam Huynh, Canton, MA (US); Per Otto Hagen, Durham, NC (US); Mark Davies, Rochester, NY (US) --

Item [63], Related U.S. Application Data, should be added to read:

--           Related U.S. Application Data
[63] Provisional application No. 60/088,198, filed on Jun. 5, 1998 --.

<u>Column 20,, line 65 to Column 21, line 9,</u>
Should read:

1. A method for producing a collagen tube comprising at least one layer of processed tissue matrix of submucosal collagen of small intestine wherein the method comprises:
   (a) rolling the submucosal collagen around a mandrel and over itself at least one complete revolution to form a submucosal collagen tube of at least one layer;
   (b) drying the tube on the mandrel;
   (c) contacting the tube with a crosslinking agent to crosslink the collagen;
   (d) removing the crosslinking agent by rinsing the tube;
   (e) drying the crosslinked tube on the mandrel; and,
   (f) removing the tube from the mandrel.

Signed and Sealed this

Sixteenth Day of March, 2004

JON W. DUDAS
*Acting Director of the United States Patent and Trademark Office*